United States Patent [19]

Hart

[11] 4,388,296

[45] Jun. 14, 1983

[54] ENERGY-EMITTING LATEX-PARTICULATES

[76] Inventor: Hiram Hart, 3450 Wayne Ave., Bronx, N.Y. 10467

[21] Appl. No.: 192,428

[22] Filed: Sep. 29, 1980

Related U.S. Application Data

[63] Continuation-in-part of Ser. No. 890,325, Mar. 27, 1980, Pat. No. 4,271,139.

[51] Int. Cl.$^3$ .................... A61K 43/00; G01N 33/56; G01N 33/60
[52] U.S. Cl. ........................................ 424/1; 252/645; 436/533
[58] Field of Search ............... 424/1, 12; 23/230 B; 252/645

[56] References Cited

U.S. PATENT DOCUMENTS 4,271,139  6/1981  Hart ........................................ 424/1

OTHER PUBLICATIONS

Hart et al., J. Nucl. Med., 20 (10) 1979, 1062–1065.

*Primary Examiner*—Christine M. Nucker
*Attorney, Agent, or Firm*—Holland, Armstrong, Wilkie & Previto

[57] ABSTRACT

This invention relates to improved energy-emitting latex-particulates for use in a non-destructive method of biological assay, wherein the biological material under assay links the distinct and different particulates in such a manner that their proximity results in a detectable signal which is indicative of the amount of such biological material present in the fluid.

More particularly, this invention relates to improved energy-emitting latex-particulates which have improved stability, a greatly extended shelf-life, particularly in the fluid suspension state, and whose use in the quantitative assay of immunological material results in a reduced background signal and improved sensitivity and stability.

8 Claims, No Drawings

ENERGY-EMITTING LATEX-PARTICULATES

This is a continuation in part of the patent application of Hiram Hart, Ser. No. 890,325, filed Mar. 27, 1980 now Pat. No. 4,271,139.

BACKGROUND OF THE INVENTION

In the cited patent application of Hiram Hart, a method is described for the quantitative determination of a biological-material in a fluid, particularly the amount of antibodies or antigens present in a immunological fluid under assay. To obtain the degree of sensitivity and accuracy desired, it had been found necessary, for some instances, to utilize reagents of relative freshness. For instance, when the reagents were prepared well in advance of the actual use in the cited quantitative procedure, it was found that in some cases, the magnitude of the assay signal was reduced. This was compounded by a significant background signal arising from fluorescence of the polystyrene of which the tritiated particles are composed. Needless to say, these effects in some cases, mask or interfere with the response desired, i.e.; a detectable light-signal which could be correlative to the amount of biological-material present in the fluid under assay. Clearly, with both these inherent difficulties present, the accuracy and sensitivity of the process were placed in jeopardy. To be sure, however, when the reagents were immediately prepared, prior to use, the accuracy and sensitivity of the cited method was maintained at a very high and acceptable level. Again, however, if a substantial length of time had expired between preparation and use, the utility of the method was placed, in some instances, in issue.

For instance, when the scintillating latex-particulates were used in the quantitative method described in the cited patent application of Hiram Hart, it was found that the supernatant of an aqueous suspension which had been standing at room temperature, for several days, was often slightly opalescent. The particles themselves had become less effective scintillators. As a result of this temperature dependent effect which is attributed to a gradual leaching of scintillant from the particles and into the medium, the accuracy and sensitivity of the analytical method as a routine laboratory procedure was placed in issue. Another difficulty, which compounded the problem, found basis in the inherent background signal of the tritiated-latex-particulates themselves. Again, in specific instances, the general utility of the process was questioned because the background signals interfered with the sensitivity and accuracy of the responsive signal in the quantitative determinative method described.

It was found, however, that the inherent properties and functions of the energy-emitting latex-particulates, which were desired, could be maintained, or highly improved, by the specific procedures of preparing them. These energy-emitting latex-particulates include both the tritiated-latex-particulates and the scintillating-latex-particulates. Both were prepared to enhance their use in the cited quantitative procedure. As a result, the signal desired was clearly defined, responsive to activation, and quatitatively correlative to the presence in the fluid of an exact amount of biological-material under assay, and these features were readily obtained by methods of preparing the particulates themselves. The effects were accomplished by the elimination of the background masking of the desired responsive signal which occurred with the production of opalescence and significant background signals both of which were inherent in the use of some of the particulates themselves.

It is therefore an object of this invention to provide energy-emitting latex-particulates which do not exhibit masking effects on the quantitative signal, whether physical or chemical when used in the non-destructive method of assay of biological materials, particularly the assay of immunological materials such as antibodies and antigens.

A further object of the invention is to provide scintillant latex particulates having inherent stability, and a greatly extended life when in the fluid suspension state.

Another object of this invention is to provide improved tritiated latex particulates with the responsive signal indicating the quantity of immunological material in the fluid under assay.

DESCRIPTION OF THE PREFERRED EMBODIMENT

In general, commercially available latex-particulates which were substantially uniform have been utilized in the preparation of the energy-emitting particles with highly acceptable results being achieved as a result of the processing techniques. In one case, the latex-particulates were tritiated and then impregnated with a substituted benzotriazole to reduce the background scintillations arising from the tritiated particles themselves. As a result the tritiated particulates exhibited negligible scintillation count rates in aqueous suspensions containing no scintillant particles. In another case, the latex-particulates, heretofore described, are impregnated with PPF (2,5-Diphenyfluran) and bis-MSB (p-bis(O-methylstyryl) benzene) resulting in scintillant particles exhibiting long term high sensitivity and stability in aqueous suspensions.

In either case, after developmental processing, the energy-emitting latex-particulates possessed stability, exhibited extended shelf-life particularly in the field state, and acting in conjunction produced clear, distinct signals which were not masked and which were correlative to the quantity of biological material present in the fluid under assay in a highly accurate and sensitive manner. In other words, the processed energy-emitting latex-particulates were enhanced in effectiveness and efficiency in use.

METHOD OF PREPARATION

A. Tritiated-Latex-Particulates

Latex particulates having an average diameter of about $0.920\mu$ whose surfaces were previously carboxylated with known procedures, were tritiated by the Wilzbach procedure as set forth in J. Am. Chem. Society 79, 1013, 1957, and Advances in Tracer Methodology Vol. 1, page 4, Plenin Press, New York, 1963, 0.7 ml. of an aqueous suspension containing 28 mg. of tritiated latex particles was added to 0.06 ml. of benzene containing 2 mgm of a substituted benzotriazole which is commercially available from Ciga-Geigy under the tradename Tinuvin P. The mixture was rendered homogeneous, and evaporated under a partial vacuum at room temperature. The resulting particles were found to be ready for immediate use in the analytical procedure if it were necessary. In fact, however, the tritiated-latex-particulates above were used over an extended period of time in the cited procedure or method of analytical determination of immunological materials, particularly antibodies and antigens.

It was found that the scintillant count rate for such Tinuvan P impregnated tritiated latex particles in aqueous suspension was many fold less than the scintillant count rate of the same concentration of tritiated particles which had not been impregnated with benzotriazoles. As a result, the detectable response in the form of a light-signal from the scintillating-latex-particulates was not as subject to significant interference, and the detectable response achieved was more readily correlative to the amount of immunological material in the fluid under assay.

B. Scintillating-latex-particulates:

0.6 ml. of an aqueous suspension containing about 60 mg. of surface carboxylated latex-particulates having an average diameter of about $0.920\mu$ were added to 0.2 ml. of benzene containing about 6 mg. of 2.5-diphenylfuran and about 0.06 mg. of p-bis (o-methylstrylryl) benzene. The resulting mixture was rendered homogeneous, and evaporated under a partial vacuum at room temperature. The resulting scintillating-latex-particulates were ready for use, and were also found highly stable, with a greatly improved shelf-life, and quite effective and efficient when used in the cited non-destructive process of the cited Hiram Hart application.

METHOD OF USE

The energy-emitting latex-particulates of this invention were used in accordance with the method of preparation and use of the latex-particulates described in the cited Hiram Hart application. The procedure of preconditioning of the particles, and the actual procedures for the use of such particulates in the quantitative method of analysis for both antibodies and antigens are incorporated herein by reference.

In the use of the cited method of analysis, it was found that the sensitivity of the method was increased to the detection of antigen titers of $10^7$ from titers of $10^6$ as set forth in the cited patent application. The underlying or basic reason for this achievement was in the use of the energy-emitting latex-particulates of this invention, which were prepared as heretofore described. It is evident from these actual tests, and the results obtained, that this is clearly advantageous. This is especially the case if the method of the cited Hart application is hereafter automated.

STORAGE

To facilitate ease of storage, and availability in a form easy to use, the two energy-emitting latex-particulates may be separably coated on a pill or pills for ready dispersion in a fluid medium. In other words, the dry coatings on the dry substrate could be stored for an extended length of time without loss of stability. When desired, the coated pills or tablets would be introduced into the fluid medium in the conventional manner. The coating composed of energy-emitting latex-particulates would upon submission, disperse from the surface of the pill which can be soluble and form a suspension of both tritiated-latex-particulates and scintillating-latex-particulates, and in such state, both being readily available for use in the quantitative determination of the presence of the biological-material in such fluid under assay by the non-destructive method cited.

It has been found however, that the energy-emitting latex-particulates may be maintained in the suspended state in an aqueous fluid for an extended time, in some cases greater than 11 months, without loss of stability. At the end of the period, the materials were found to be effective and efficient in use in the cited method of quantitative analysis.

In general, it is to be noted, that in order for the tritiated-latex-particulate to be quantitative responsive to the linkage, and thus to the amount of material in the fluid under assay, it must be within the zone of activation. Also the scintillating particulate will not give off detectable signals or pulses of any great concern until it is activated by the energy from the tritiated-latex-particulate. Needless to say, if a particulate gave off any large amount of fluoresence without activation, its use in the cited process would be prohibited. In such a case, a large amount of fluorescence which was present without external activation would mask the responsive readings, and the accuracy and sensitivity of the cited method would be jeopardized.

In conclusion, the problems facing the art have been solved. The rapid degradation of the scintillant particulates at room temperature in a matter of days, when in dilute suspension, has been eliminated. In the past, the procedures in some cases involved oven-drying in the preparation of the latex-particulates or substrates. As a result, it was found that the energy-emitting latex-scintillant-particulate gave off an insignificant responsive signal, if it gave any at all, when used in the cited analytical procedure. This was a result of the oven-drying of the reagents during preparation. This problem no longer exists. The energy-emitting latex-particulates of this invention are always efficient and effective in use in the cited analytical procedure.

The problems associated with background counts arising from the tritum activated fluoresence of the polystyrene of the tritiated particles have been grossly reduced.

The responsive light-pulse is not subject to significant interference, and the signal is clear, distinct, and readily correlative quantitatively to the biological material in the fluid under assay. The scintillating-latex-particulate which has been developed, as heretofore described, can be provided with proper cross-section for photon production of an acceptable order when activated by low-energy beta-ray exposure from the tritiated-latex-particulate. An acceptable order means the photons produced can be readily correlative to quantity or amount of biological material being measured in the fluid. The particulates are highly soluble in benzene (i.e.; benzene is highly soluble in the particulates) and possess low solubility in water, and both these physical properties contribute to facile preparation, processing, and use. The tritiated-latex-particulate, prepared as taught, had a negligible background signal by itself, if any at all. Results indicate such inherent disadvantages were reduced by a factor greater than 4, and sensitivity of the quantitative process in which such particulates were used were improved to an antiserum titer of $10^7$ from a titer of $10^6$. Actual testing already indicates the shelf-life of the scintillant-latex-particulates to be greater than 11 months, or maybe longer, rather than a matter of days as was experienced with some of the reagents of the art. And, even after this greatly extended time of shelf-life, the reagents were found to be efficient and effective in use and not accompanied by any meaningful reduction in sensitivity during this period of storage.

I claim:

1. Improved energy-emitting latex particulates for use in the non-destructive method of biological fluid assay wherein biological material being assayed links fluid suspensions of both a plurality of tritiated latex particulates and potentially scintillating latex particulates within activating range one to the other, each of said scintillating latex particulates emitting detectable light pulses upon activation responsive to bombardment of energy from each of said linked tritiated latex particulates within said range, said light pulses being quantitatively correlative to the concentration of said biological material in said fluid, the improvement wherein said tritiated latex particulates, having a polystyrene base with benzotriazole, coated covalently with an antibody, and said scintillating latex particulates having a polystyrene base with 2,5-diphenylfuran and p-bis ($\alpha$-methylstyrl) benzene, coated covalently with an antibody.

2. Improved energy emitting latex particulates for use in the non-destructive method of biological fluid assay wherein biological material being assayed links fluid suspensions of both a plurality of tritiated latex particulates and potentially scintillating latex particulates within activating range one to the other, each of said scintillating latex particulates emitting detectable light pulses upon activation responsive to bombardment of energy from each of said linked tritiated latex particulates within said range, said light pulses being quantitatively correlative to the concentration of said biological material in said fluid, the improvement wherein said tritiated latex particulates, having a polystyrene base with benzotriazole, coated covalently with an antigen, and said scintillating latex particulates, having a polystyrene base with 2,5-diphenylfuran and p-bis ($\alpha$-methylstyryl) benzene, coated covalently with an antigen.

3. Improved energy emitting latex particulates comprising tritiated latex particulates coated covalently with an antibody and having a polystyrene base and containing benzotriazole.

4. Improved energy emitting latex particulates comprising scintillating latex particulates coated covalently with an antibody and having a polystyrene base and containing 2,5-diphenylfuran and p-bis ($\alpha$-methylstyryl) benzene.

5. Improved energy emitting latex particulates comprising tritiated latex particulates coated covalently with an antigen and having a polystyrene base and containing benzotriazole.

6. Improved energy emitting latex particulates comprising scintillating latex particulates coated covalently with an antigen and having a polystyrene base and containing 2,5-diphenylfuran and p-bis ($\alpha$-methylstyryl) benzene.

7. An improved energy emitting latex particulates comprising a core of separable layers, one of said layers tritiated latex particulates coated covalently with an antibody and having a polystyrene base and containing benzotriazole, the other of said layers potentially scintillating latex particulates coated covalently with an antibody and having a polystryene base and containing 2,5-diphenylfuran and p-bis ($\alpha$-methylstyryl) benzene.

8. An improved energy emitting latex particulates comprising a core of separable layers, one of said layers tritiated latex particulates coated covalently with an antigen and having a polystyrene base and containing benzotriazole, the other of said layers potentially scintillating latex particulates coated covalently with an antigen and having a polystryene base and containing 2,5-diphenylfuran and p-bis ($\alpha$-methylstyryl) benzene.

* * * * *